(12) United States Patent
Kelsch et al.

(10) Patent No.: US 6,482,358 B1
(45) Date of Patent: Nov. 19, 2002

(54) THREE PART CUP FOR PACKAGING CLEANING AND STERILIZING AGENTS AND SEQUENTIAL CUTTER

(75) Inventors: Daniel N. Kelsch, Fairview Park; Jude A. Kral, Twinsburg; Joseph Tvcrgyak, Chardon; Bernard J. Moss, Willowick; James C. Hlebovy, Chardon, all of OH (US); Arthur T. Nagare, Erie, PA (US); Jeffery R. Horacek, Mentor, OH (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 09/499,241

(22) Filed: Feb. 7, 2000

(51) Int. Cl.[7] .................................................. A61L 2/00
(52) U.S. Cl. .......................... 422/28; 134/93; 134/95.1; 137/268; 422/33; 422/292; 422/300
(58) Field of Search ............................ 422/28, 33, 292, 422/300; 134/93, 95.1; 137/268

(56) References Cited

U.S. PATENT DOCUMENTS

| | | |
|---|---|---|
| 4,590,037 A | 5/1986 | Kaye |
| 4,731,222 A | 3/1988 | Kralovic et al. ............... 422/37 |
| 5,037,623 A | 8/1991 | Schneider et al. |
| 5,209,909 A | 5/1993 | Siegel et al. |
| 5,217,698 A | 6/1993 | Siegel et al. ................ 422/295 |
| 5,439,654 A | 8/1995 | Kochte |
| 5,552,115 A | 9/1996 | Malchesky ................... 422/28 |
| 5,662,866 A | 9/1997 | Siegel et al. |
| 5,776,118 A | 7/1998 | Seifert et al. |
| 5,858,305 A | 1/1999 | Malchesky |
| 5,997,814 A | 12/1999 | Minerovic et al. |
| 6,039,724 A | 3/2000 | Seifert et al. |

Primary Examiner—Krisanne Thornton
(74) Attorney, Agent, or Firm—Fay, Sharpe, Fagan, Minnich & McKee, LLP

(57) ABSTRACT

A sequential delivery assembly (30) sequentially releases three different treatment materials into a fluid flow path (24) to form a treatment fluid with a composition which varies throughout a cleaning and microbial decontamination cycle. A chamber (12) receives items to be cleaned and decontaminated. A pump (22) pumps the treatment fluid from the sequential delivery assembly along a fluid flow line (24) to nozzles (16, 18) disposed within the chamber. The nozzles spray the treatment fluid over the items to be cleaned and decontaminated. The delivery assembly includes a well (34) for receiving a three compartment cup (44). The cup contains a first compartment (70) which includes a cleaning material (76), such as a detergent. A second compartment (72) contains pre-treatment materials (78), such as buffers and corrosion inhibitors, which prepare the system for receiving a microbial decontaminant (80), such as a concentrated solution of peracetic acid, contained in the third compartment (74). The sequential delivery assembly includes a cup cutter assembly which sequentially cuts base portions (90, 94, 118) of the three compartments to release the treatment materials into the fluid flow line. The system allows items to be cleaned and then microbially decontaminated in a single process, avoiding the need to handle potentially hazardous instruments between cleaning and decontamination steps and ensures thorough cleaning and decontamination of the instruments with measured doses of the treatment materials.

29 Claims, 11 Drawing Sheets

THREE PART CUP FOR PACKAGING CLEANING AND STERILIZING AGENTS AND SEQUENTIAL CUTTER

BACKGROUND OF THE INVENTION

The present invention relates to the decontamination arts. It finds particular application in conjunction with the sequential cleaning and microbial decontamination of medical instruments and equipment and will be described with particular reference thereto. It should be appreciated, however, that the invention is also applicable to a wide variety of technologies in which at least three components or reagents are kept separate until time of use and then sequentially released into a fluid line.

Heretofore, medical equipment and instruments have often been microbially decontaminated by sterilizing or disinfecting the equipment in a steam autoclave. Autoclaves kill life forms with a combination of high temperature and pressure. However, steam autoclaves have several drawbacks. The high temperature pressure vessels tend to be bulky and heavy. The high temperature and pressure tends to curtail the useful life of endoscopes, rubber and plastic devices, lenses, and portions of devices made of polymeric materials and the like. Moreover, a typical autoclave sterilizing and cool down cycle is sufficiently long that multiple sets of the medical instruments are commonly required.

Instruments which cannot withstand the pressure or temperature of the oven autoclave are often microbially decontaminated with ethylene oxide gas, particularly in larger medical facilities or hospitals. However, the ethylene oxide sterilization technique also has several drawbacks. First, the ethylene oxide sterilization cycle tends to be even longer than the steam autoclave cycle. Another drawback is that ethylene oxide sterilization is sufficiently sophisticated that trained technicians are commonly required, making it unsuitable for physician and dental offices and for other smaller medical facilities. Moreover, some medical equipment can not be sterilized with ethylene oxide gas.

Liquid microbial decontamination systems have recently been utilized for equipment which could not withstand the high temperatures of steam sterilization. Commonly, a technician mixes a liquid disinfectant or sterilant composition and manually immerses the items to be microbially decontaminated in the composition. The high degree of manual labor introduces numerous uncontrolled and unreported variables into the process. There are quality assurance problems with technician errors in the mixing of sterilants, control of immersion times, rinsing of residue, exposure to the ambient atmosphere after the rinsing step, and the like.

Moreover, it has recently come to light that items which have been throughly sterilized may nevertheless be contaminated with biological materials. Although sterile, these materials may break down and be converted to toxins which are hazardous to patients on which the instruments are used. Additionally, the presence of biological materials on the items reduces the efficiency of the sterilization process because the biological materials inhibit the access of the decontaminant to the microorganisms. To reduce the amounts of these toxin-producing residues and provide for more effective sterilization, items are now frequently cleaned before sterilization or disinfection. The separate cleaning step, however, can be hazardous to operators who handle the cleaned instruments and transfer them from the cleaning bath to the sterilizer.

To deliver reproducible amounts of sterilants to the microbial decontamination system, a number of packaging systems have been developed. One problem to overcome is that cleaning agents, such as detergents, and pretreatment agents, such as buffers and corrosion inhibitors, tend to degrade peracetic acid. Combining them with liquid peracetic acid results in an unacceptably short shelf life. Thus, for peracetic sterilants, in particular, such components of a treatment system are generally kept separate to prolong shelf life. U.S. Pat. No. 5,037,623 to Schneider, et al., for example, discloses a cup which contains a measured dose of a liquid peracetic acid concentrate. Buffers, detergents, and anticorrosive agents, in the form of a powder, are separately contained. The cup includes a linear vent passage which extends into the interior of the cup. A gas permeable membrane is mounted over the interior end of the vent passage to allow venting of the container during storage. The cup is only partially filled with sterilant liquid such that the top surface of the liquid is always below the vent aperture, irrespective of the orientation of the cup.

U.S. Pat. No. 5,662,866 to Siegel, et al. discloses a two-compartment cup for powdered sterilant reagent components. An outer compartment holds a first reagent while an inner compartment, disposed within the outer compartment, holds a second reagent. In the case of peracetic acid, the two reagents react in water to form peracetic acid. Pretreatment agents may be included in one of the two compartments. Peripheral walls of inner and outer cups are affixed together at flanges adjacent their open ends to define the two compartments. A permeable sheet is affixed to the inner cup flange for ventedly sealing both cups. The outer cup is closed at its base by a first detachable base and the inner cup similarly closed by a second detachable base.

To release the sterilant into the fluid flow path of a microbial decontamination system, the cup is inserted into a well in fluid communication with the system. In the case of the liquid sterilant cup, a peel-off top is removed to provide access to the contents of the cup. Alternatively, a cutter, such as that disclosed in U.S. Pat. No. 5,439,654 to Kochte, pierces the base of the cup with a blade. Jets of water are sprayed into the cup to dissolve and flush the sterilizing agents from the cup. In the case of the powdered sterilant cup, pressure is applied to detach the bases of the inner and outer cup portions.

The measured dosage cups, while improving sterilization assurance with a reproducible, pre-measured dose of reagents, release the entire contents of the cup into the microbial decontamination system at the same time. There is no provision for sequential release of other components, such as cleaning agents, corrosion inhibitors, buffers, and the like. Although such components may be included in the measured dosage cups, their effectiveness is less than if used as pretreatments. Because these are released into the system at the same time as the sterilant, they do not have time to circulate through the microbial decontamination system prior to addition of the sterilant. In the case of inhibitors, for example, their function is to provide protection for the system and items to be sterilized against the corrosive components of the sterilant. By releasing inhibitors at the same time as the sterilant, the sterilant has the opportunity to corrode metal parts before the inhibitors have developed protective barriers around the parts. In the case of buffers, their function is to modify the pH of the fluid circulating in the system so that the pH is optimal for sterilization. Until the buffer has circulated throughout the system, the sterilant is not fully effective. Additionally, such agents may degrade the sterilant during storage.

The present invention provides for a new and improved multi-compartment packaging assembly and sequential cutter which overcome the above-referenced problems and others.

SUMMARY OF THE INVENTION

In accordance with one aspect of the present invention, a combined system for selectively cleaning and microbially decontaminating items is provided. The system includes a receiving well for receiving a container which separately contains at least a first treatment material and a second treatment material, the first treatment material including a cleaning agent, the second treatment material including a microbial decontaminant. A sequential delivery assembly sequentially releases the first treatment material and the second treatment material from the container. A first fluid flow path is defined between a water receiving inlet and the well for supplying water from the inlet to the well to mix with the first and second treatment materials to form a treatment fluid. The treatment fluid sequentially includes the first treatment material and the second treatment material. A second fluid flow path is defined for the treatment fluid from the well to a cleaning and decontaminating region for receiving items to be sequentially cleaned and microbially decontaminated. A fluid circulator selectively circulates fluid through the first and second fluid flow paths and among the decontamination region and the receiving well.

In accordance with another aspect of the present invention, a method of sequentially cleaning and decontaminating items is provided. The method includes opening a first compartment of a container to release a first treatment material, mixing the first treatment material with water to form a first treatment fluid, and delivering the fluid to a cleaning and decontaminating region containing the items to be cleaned and decontaminated. The items are contacted with the first treatment fluid for a period sufficient to clean substantially the items. The method further includes opening a second compartment of the container to release a second treatment material, mixing the second treatment material with a mixing fluid, which includes water, to form a second treatment fluid, and delivering the second treatment fluid to a cleaning and decontaminating region containing the items to be cleaned and decontaminated. The items are contacted with the treatment fluid for a period sufficient to decontaminate them.

In accordance with yet another aspect of the present invention, a sequential delivery system is provided. The system includes a receiving well for receiving a multi-compartment container. The container includes first, second, and third compartments, each defining a peripheral wall, which receive first, second, and third materials, respectively. A sequential cutter selectively cuts the first, second, and third peripheral walls. A fluid flow path in fluid communication with the sequential cutter selectively delivers a dilution fluid to the first, second, and third compartments to flush out the first, second, and third materials.

In accordance with another aspect of the present invention, a three compartment cup for use in a decontamination system of the type which includes a decontamination chamber for receiving items to be cleaned and decontaminated and a decontaminant receiving well in fluid communication with the chamber, is provided. The cup includes first, second, and third cup portions, each including a peripheral wall which define first, second, and third compartment. First, second, and third treatment materials are disposed in the three compartments. The first treatment material includes a cleaning material, the second treatment material including a pretreatment material for preparing the decontamination system for receiving a decontaminant. The decontaminant is disposed in the third compartment. The first, second, and third compartments are configured for sequential opening of the first, second, and third peripheral walls.

One advantage of the present invention is that it facilitates materials handling.

Another advantage of the present invention is that it simplifies filling and sealing of cleaning agents, sterilizing reagents, and pretreatment reagents in separate compartments.

Yet further advantages of the present invention derive from the sequential cleaning and sterilization of items in a single system.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
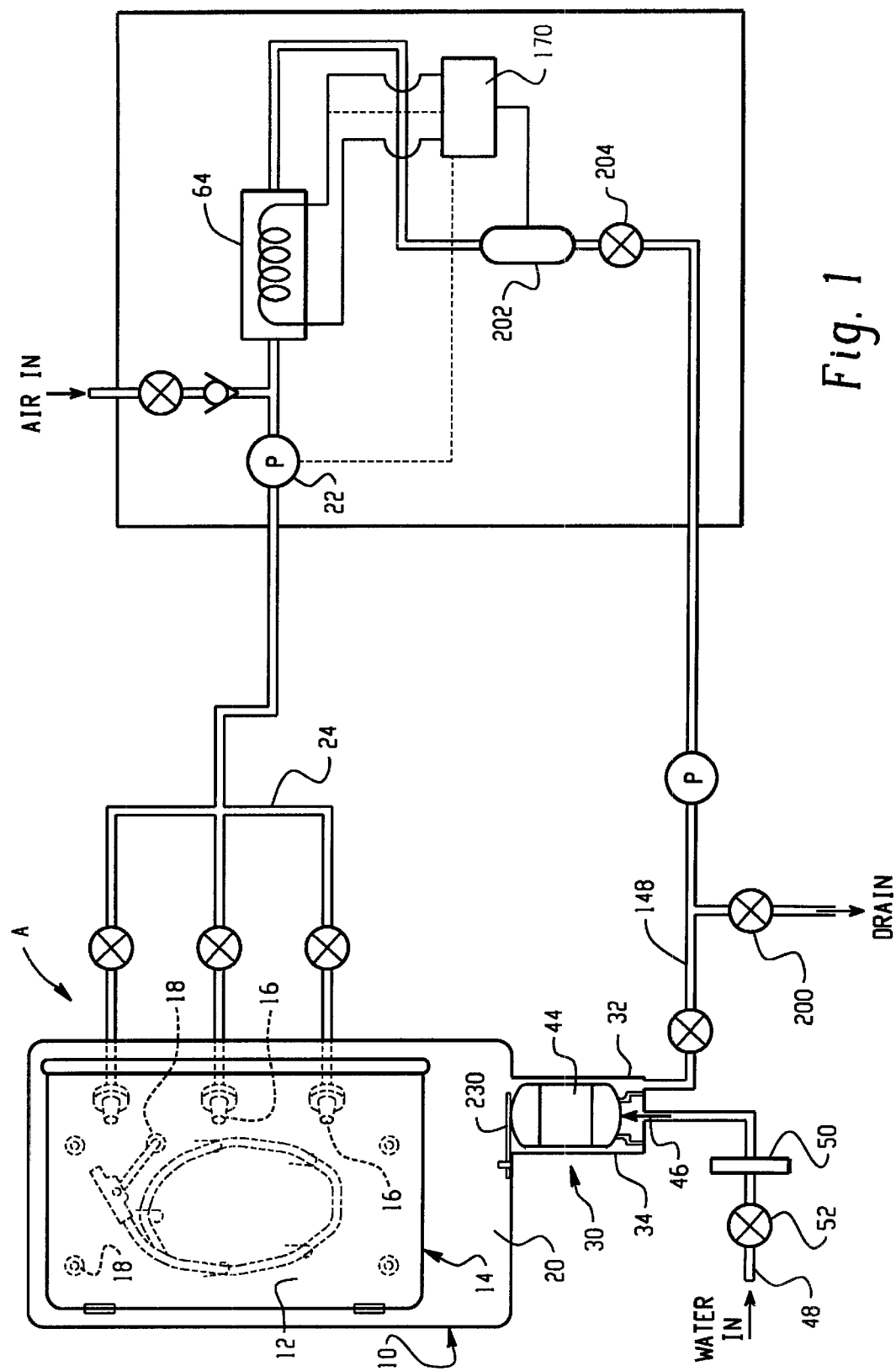
FIG. 1 is a plumbing diagram of the decontamination unit of FIG. 1 including a cross-sectional view of a sequential delivery assembly and a three-compartment reagent cup.

With reference to FIG. 1, an automated liquid system for first cleaning and then sterilizing or disinfecting of medical and pharmaceutical instruments, and the like is shown. The system includes a decontamination cabinet 10 which defines an interior chamber 12. Items to be cleaned and sterilized or disinfected are loaded into the chamber through a door 14 in a wall of the decontamination cabinet. Within the chamber, spray jets or nozzles 16 spray a treatment fluid over the items. Some of the nozzles 18 are adapted for interconnection with internal passages of endoscopes and other objects with lumens. The composition of the treatment fluid changes throughout a processing cycle. Accordingly, the treatment fluid includes, at progressive stages of the cycle, different treatment materials, such as cleaning and rinsing agents, pretreatment agents, and liquid sterilants or disinfectants (herein jointly referred to as decontaminants).

A collection tank or sump 20 at the base of the cabinet 10 receives the sprayed treatment fluid as it drips off the items. A pump 22 delivers the treatment fluid under pressure to the nozzles 16,18 through a fluid distribution system 24 optionally, in the case of instruments with lumens, or other internal passages, the fluid inlet line is also connected to the internal passages so that the treatment fluid contacts interior surfaces of the items as well as the exterior surfaces. A sequential delivery assembly 30 releases the treatment materials at appropriate times. The assembly 30 is in fluid communication with the fluid distribution system 24.

The delivery assembly 30 includes a cylindrical reservoir 32 which defines a well 34 for receiving the concentrated treatment materials. A disposable three-compartment container or cup 44 is positioned in the well. The cup holds measured doses of the treatment materials, such as concentrated cleaning agents, decontaminants, and pretreatment agents. The delivery assembly also includes a cup cutter assembly 46 which sequentially opens the three compartments.

As shown in FIG. 1, the delivery assembly is integral with the sump 20, although it is also contemplated that the delivery system be located elsewhere in the system, in fluid communication with the fluid distribution system 24.

A water inlet line 48 fluidly connected with the well 34 delivers fresh water to the system to provide a dilute solution of one or more of the treatment materials. The water used may be tap water or treated water, such as distilled water. The quantity of water entering the system is regulated to provide a treatment fluid of a desired concentration of the treatment material or materials passing through the chamber 12. The water is passed through a microporous filter 50 in the water inlet line 48 which filters out particles of dirt and microorganisms. A valve 52 in the water inlet line 48 closes when the desired quantity of water has been admitted. The water enters the well through the cup cutter assembly 46.

A heater 64 situated in the fluid distribution system 24 heats the treatment fluid to a desired temperature for effective cleaning or decontamination. The fluid distribution system returns the sprayed treatment fluid from the sump 20 to the nozzles 16, 18. At least a portion of the sprayed fluid is first directed through the well 34. This ensures thorough mixing of the treatment materials in the fluid and dissolution of any solid components before returning the fluid to the nozzles.

Figure 2:
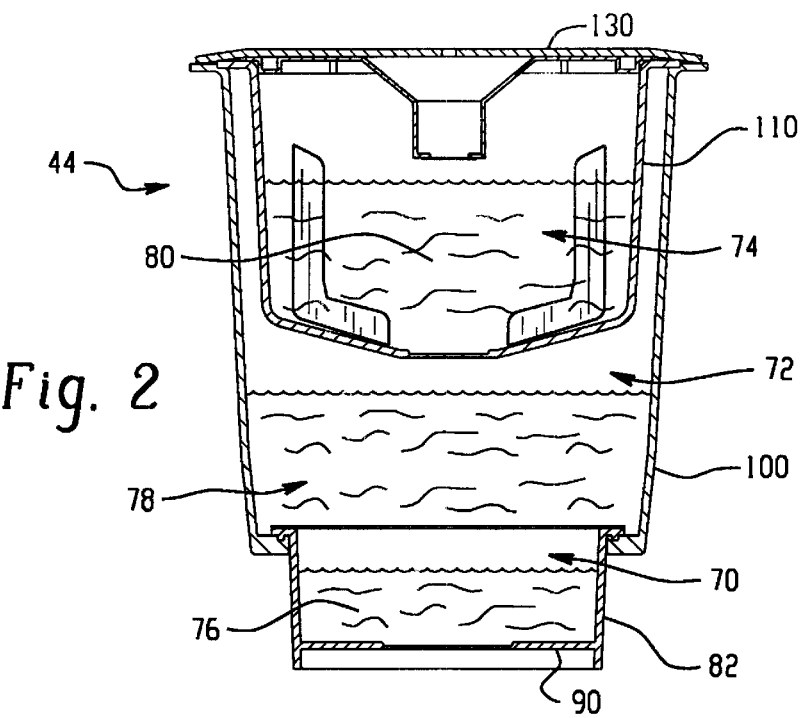
FIG. 2 is an enlarged cross-sectional view of the three compartment cup of FIG. 1.
Figure 3:
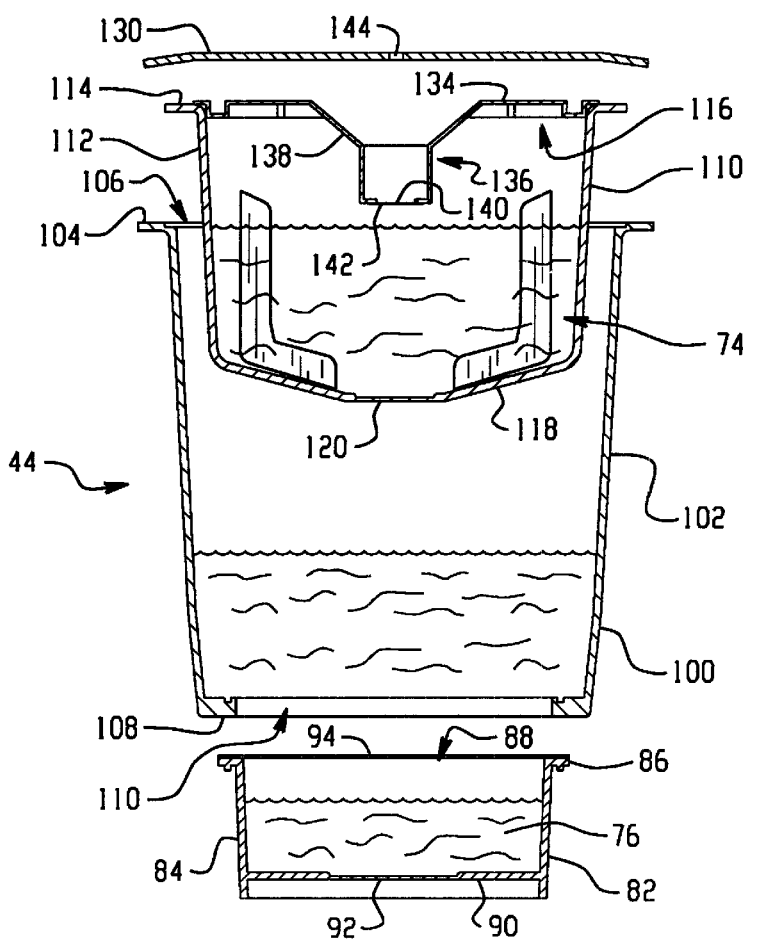
FIG. 3 is an exploded cross-sectional view of the three compartment cup of FIG. 2.

With reference now to FIGS. 2 and 3, the three compartment cup 44 includes a first compartment 70, a second compartment 72, and a third compartment 74, which are stacked one on top of the other. The first compartment 70 contains a measured dose of a first treatment material 76, which is preferably a concentrated cleaner, such as a liquid detergent. The detergent helps to remove dirt from the items in the chamber which could otherwise limit the penetration and effectiveness of the decontaminant.

The intermediate compartment 72 contains a measured dose of a second treatment material 78. The second treatment material preferably includes pretreatment agents which prepare the system for the subsequent influx of a decontaminant. Preferred pretreatment materials include, but are not limited to buffers, for buffering the circulating treatment fluid to a select pH, preferably near neutral, for optimum operation of the decontaminant, and corrosion inhibitors, for protecting the components of the system and items to be sterilized from corrosion by the decontaminant. The second treatment material 47 may be a liquid or a solid, such as a powdered mixture of inhibitors and buffering agents.

The inner compartment 74 contains a measured dose of a third treatment material 80, preferably the decontaminant. The decontaminant is optionally in the form of a concentrated solution, such as an aqueous peracetic acid solution at about 30% peracetic acid by weight, although other liquid or solid sterilants and disinfectants are also contemplated. The inner compartment may also contain materials which help to stabilize the decontaminant during storage. The sizing of the three compartments is determined by the volumes of the three components to be used, and by other factors, which will be discussed further.

FIGS. 2 and 3 show one preferred embodiment of the three compartment cup 44 in which the three compartments 70, 72, 74 are defined by three stacked cup portions. It should be appreciated, however, that the three separate compartments may be defined by any means which allows the three treatment materials to be separately and sequentially released.

A first, or lower cup portion 82 defines the first compartment 70. The first cup portion includes a cylindrical peripheral wall 84 with a flange 86 adjacent a first open end 88 thereof, and a base portion 90 which seals a second open end of the cylindrical wall 84. The base portion includes a thinned central region 92, which is readily penetrated by the cup cutter. Once the lower cup has been filled with the concentrated cleaner 76, a lid 94 is sealed over the opening 88 in the first cup.

A second, or intermediate cup portion 100 defines the second compartment 72. The second cup portion includes a cylindrical peripheral wall 102, with a flange 104 adjacent a first open end 106 thereof, and an annular base portion 108 adjacent a second open end 110 thereof. The second open end 110 receives the first cup portion 82 therethrough, with the first cup portion flange 86 engaging the annular base portion. The flange 86 and annular base portion 108 abut and are sealed together. The lid 94 of the first cup portion thus forms a base for the second cup portion 100.

A third, or inner cup portion 110 defines the third compartment 74. The third cup portion 110 is received within the second cup portion 100. The third cup portion 110 includes a cylindrical peripheral wall 112, with a flange 114 adjacent a first open end 116 thereof, and a base portion 118 which seals a second open end of the cylindrical wall 112. The base portion 118 includes a thinned central region 120 for ease of entry of the cup cutter.

The three cup portions are preferably formed from a lightweight rigid polymeric material, such as polypropylene.

The flanges 104 and 114 of the second and third cup portions 100, 110 abut and are sealed together. A top cover 130 is preferably sealed to a top surface of the third cup flange 114. Appropriate sealing methods for joining the flanges 104, 114 and top cover and the first cup flange 86 and annular base 108 include heat welding, adhesive bonding, solvent welding, ultrasonic welding, and the like.

Preferably, when the third compartment 74 contains a liquid 80, such as peracetic acid, the third cup portion 110 is sealed at its open end 116 by an inner cover 134 which is sealed to an upper surface of the flange 114 as shown in FIG. 3.

Peracetic acid solution and other strong oxidants end to outgas during storage. Accordingly, the inner cover 134 preferably includes a venting system 136 for releasing the buildup of gas. The venting system includes a vent passage 138, which is defined in a central region of the inner cover 134. The vent passage extends axially into the inner compartment 74. An opening 140 is defined in a distal end of the vent passage. Preferably, the opening is positioned to be at about the geometric center of the inner compartment 74. The peracetic acid, or other liquid decontaminant, occupies less than half of the volume of the inner compartment 74. Thus, irrespective of the orientation of the cup 44, the liquid level is always below the opening 140.

To protect against leakage due to splashing, a gas permeable and substantially liquid impermeable membrane 142 is mounted over the opening 140. Gas from the third compartment 74 passes through the membrane 142 and exits the cup 44 through a small opening 144 or permeable portion in the top cover 130. The opening may be formed by cutting a slit in the top cover or by using a porous material, such as Tyvek™, for the top cover.

The membrane 142 is formed from a fine woven material or felt which has a median pore size sufficiently small compared to the drop size and wetting ability, or surface tension, of the decontaminant that the decontaminant is effectively blocked from passing through. The decontaminant is thus retained in the third compartment, 74 until the inner cup portion base 118 is opened by the cutter assembly 46. Additionally, the cup 44 may be removed from the well 34 without danger of spillage of the decontaminant if the cycle is prematurely aborted before the third cup portion base 118 is opened.

To assemble the cup, the first and third cup portions 82, 110 are filled with their respective components, 76 and 80, and the lids 94 and 134 sealed over the upper openings 88 and 116, respectively. Then the first cup 82 is lowered into the annular base 108 of the second cup and the flange 86 sealed to the annular base. The second cup 100 is then filled with the second cup components 78. Finally, the two flanges 104 and 114 and top cover 130 are welded together to complete the cup 44.

Figure 4:
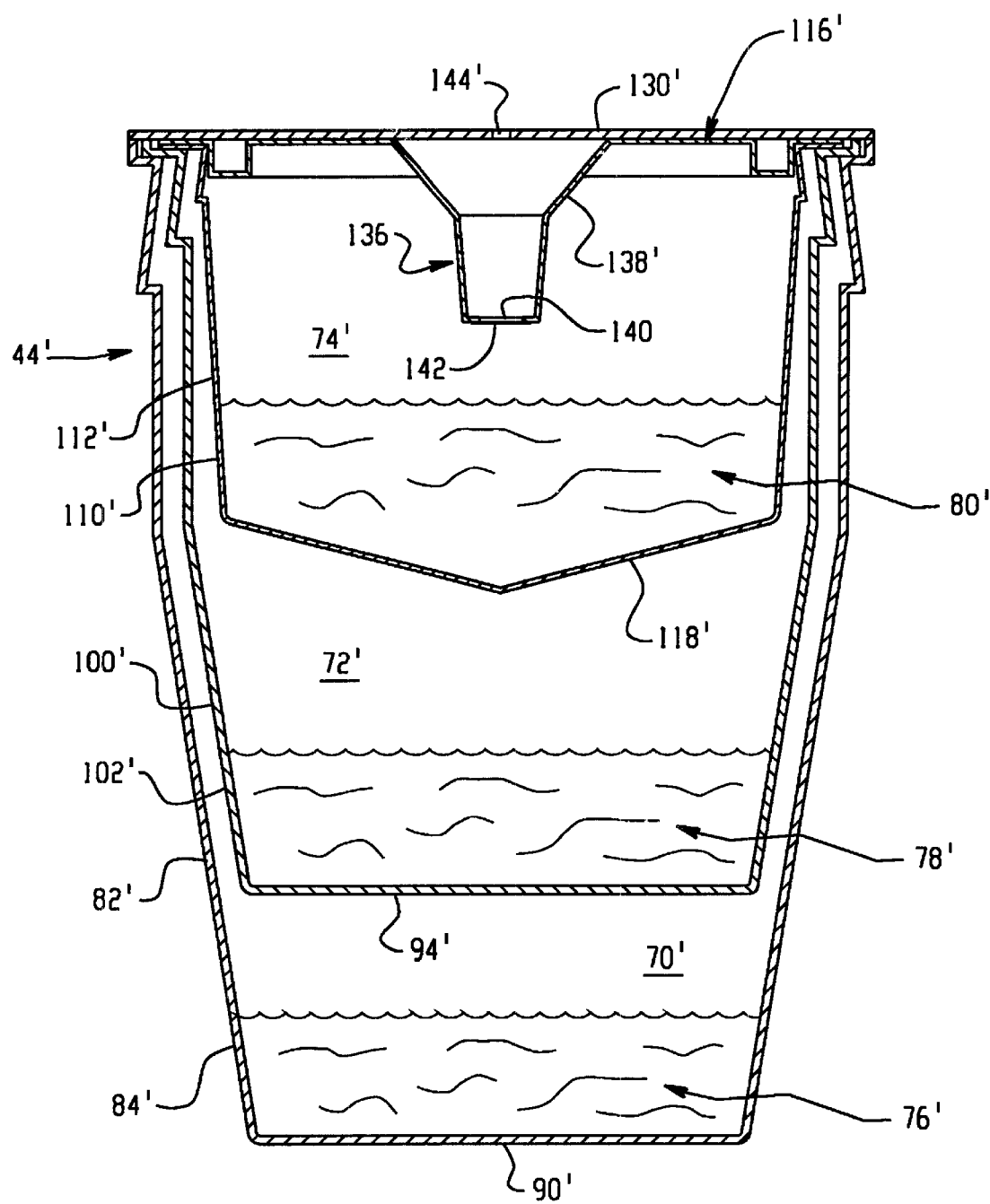
FIG. 4 is an enlarged cross-sectional view of an alternative embodiment of the three compartment cup of FIG. 1.

In an alternative embodiment, shown in FIG. 4, a three compartment cup 44' includes three stacking cup portions 110', 100', and 82', which are stacked one inside the other with flanges 114', 104', and 86', respectively. The three flanges are sealed together with a lid 130' at an upper end of the cup 44'. The three compartment cup 44' is similar, in many respects, to the cup 44 of FIGS. 2 and 3, except in that the first cup 82 surrounds the second and third cups 100', 110', rather than being seated in the second cup base. Thus, in this embodiment, each cup has its own integral base 118', 94', and 90', which closes off the lower end of a cylindrical side wall 112', 102', and 84', respectively. The inner cup 110' has a venting system 136', analogous to that of the cup 44 of FIGS. 2 and 3.

To assemble the three compartment cup 44', the third treatment material (e.g., peracetic acid) is inserted into the third, or inner compartment 74' and the inner cover 134' sealed to the flange 114' to close the open end 106' of the compartment. The first treatment material (e.g., a concentrated cleaner) is inserted into the first compartment 70' and the first and second compartment flanges are sealed together, thereby sealing the first treatment material in the first compartment. The second treatment material (e.g. buffers, corrosion inhibitors, and the like) is inserted into the second compartment 72'. The flange of the third compartment 74' is then sealed to the second cup thereby sealing the second treatment material in the second compartment 72'. Finally, the top cover 130' is sealed to the second or third compartment flange, defining an air space between the top cover and the inner cover 134. The above described method of assembling the cup avoids accidental intermixing of the three treatment materials during assembly. Other methods of assembling the cup are also contemplated.

Figure 5:
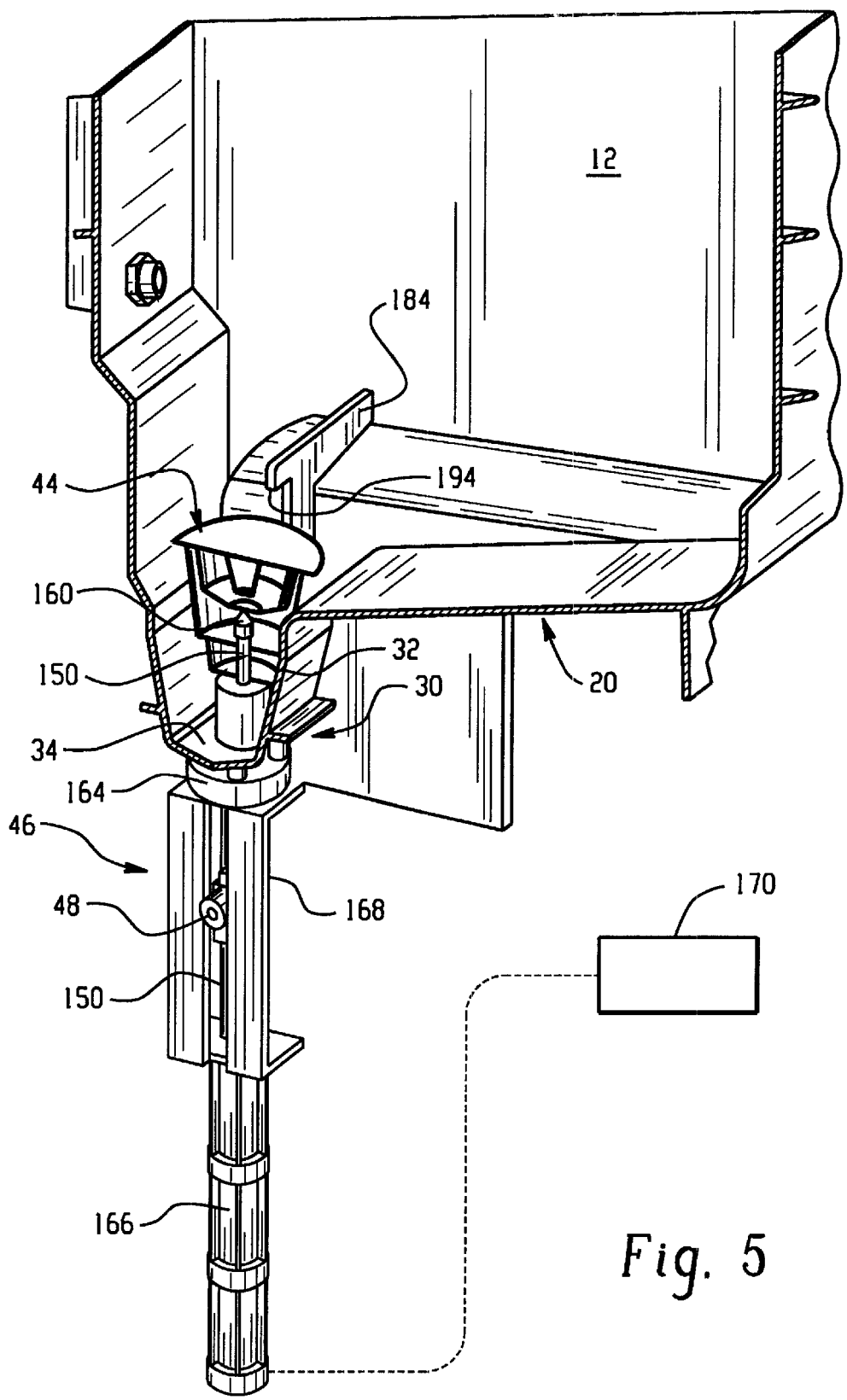
FIG. 5 is an enlarged perspective view of the receiving well, three compartment cup, and cutter of FIG. 1 with the cup restraining member removed.
Figure 6A:
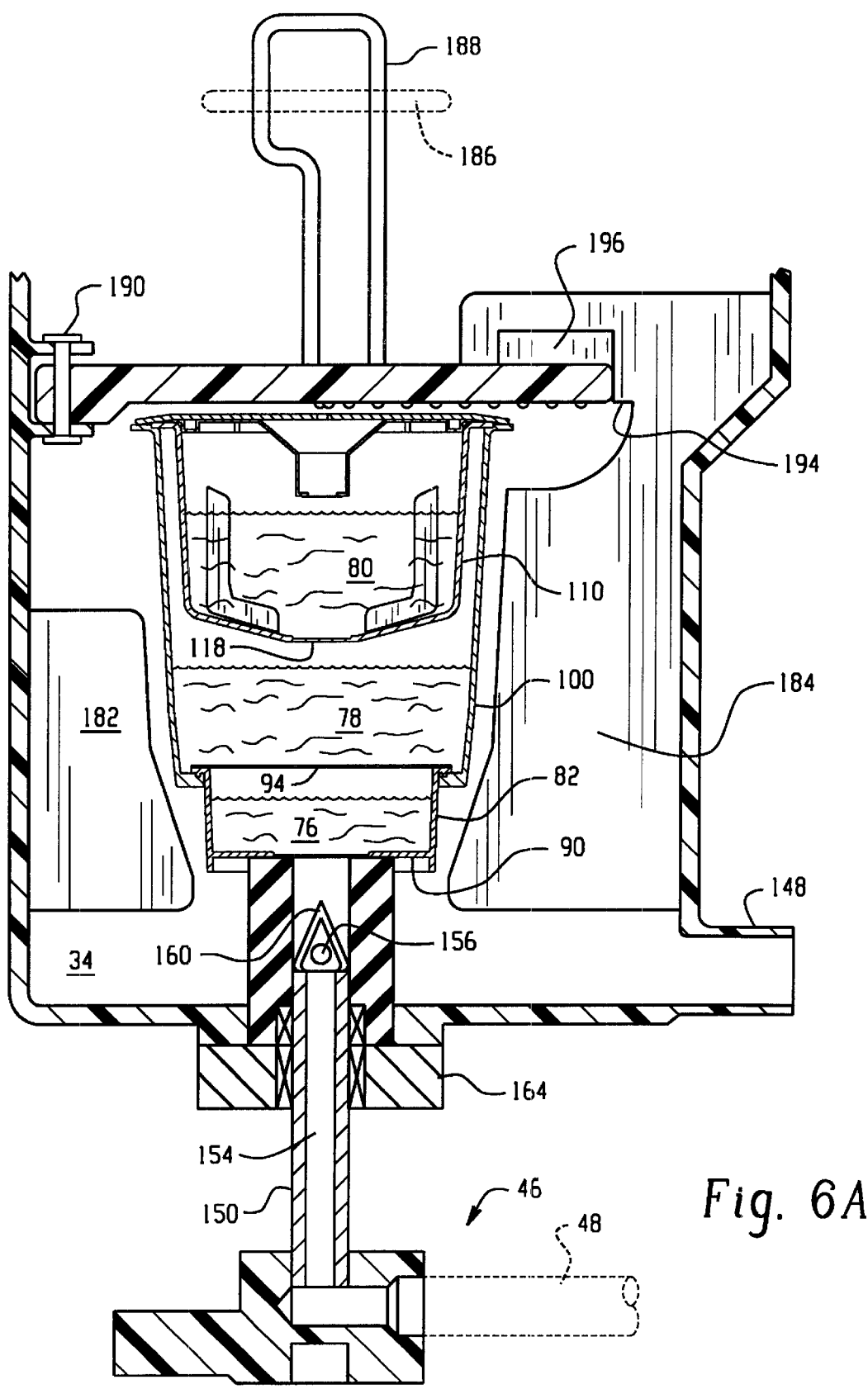
FIG. 6A is an enlarged cross-sectional view of the receiving well, three compartment cup, and cutter of FIG. 1.
Figure 6B:
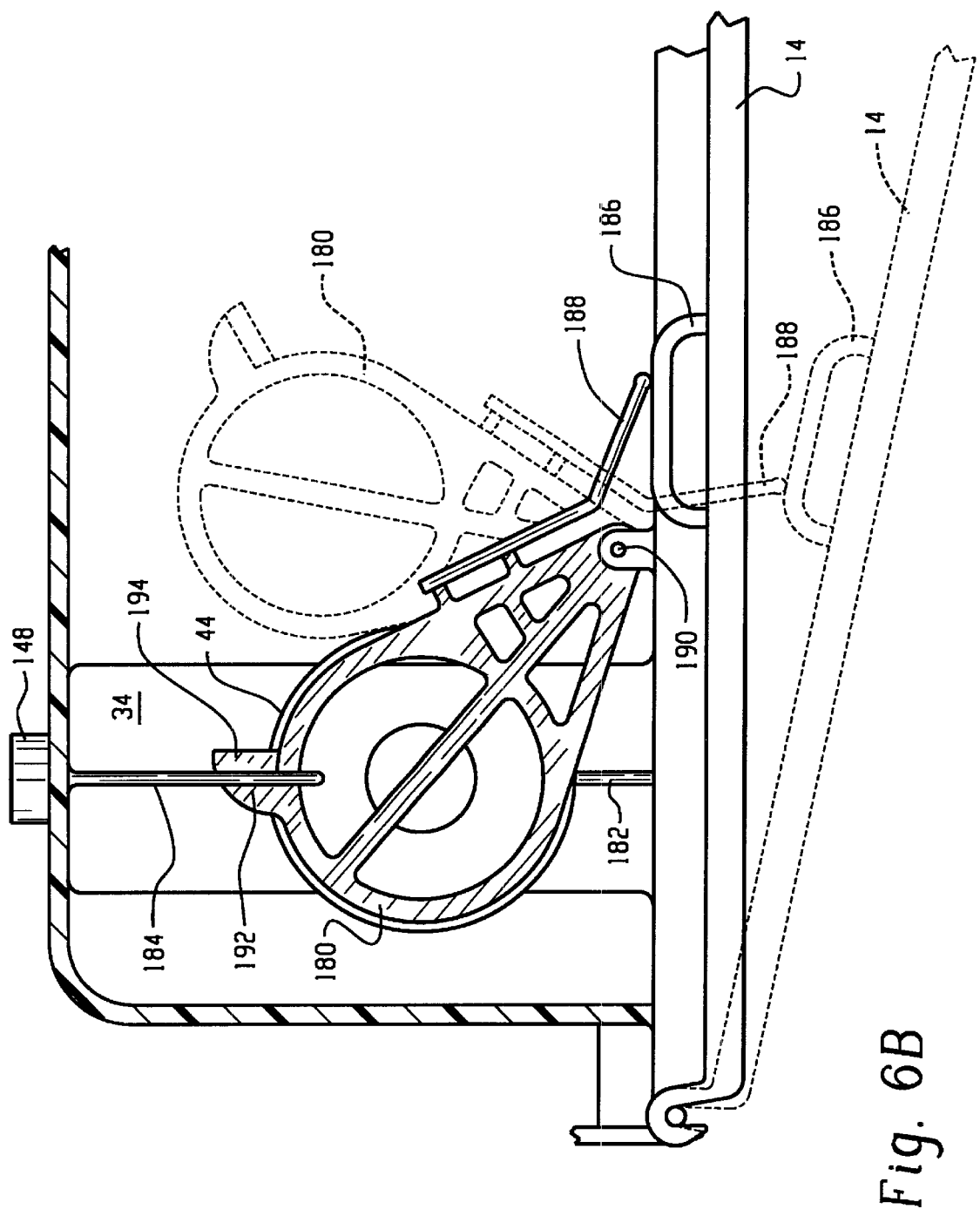
FIG. 6B is a top view of the well of FIG. 6.

With reference now to FIGS. 5, 6A and 6B, the cup cutter assembly 46 sequentially cuts the bases 90, 94, and 118 of the three cup portions 82, 100, 110, respectively, to release the contents of each compartment into the well 34. The contents are carried out of the well into the fluid circulation system 24 via a return line 148. The cutter assembly includes one or more generally cylindrical cutting shaft(s) 150. The cutter assembly is positioned such that the shaft 150 moves upwards into the well 34, through an opening 152 in a base portion thereof. The shaft extends along the central vertical axis of the well, and is aligned with the central thinned regions of the first and third cups. Alternatively, two or more shafts are positioned side by side, to cut each base in two positions.

The shaft 150 defines a hollow interior passage or bore 154 in fluid communication with the water inlet line 48. Two or more apertures 156 are located on opposite sides of the shaft. The apertures progressively direct jets of water into each of the three compartments 82, 100, 110 of the cup 44 as each base is cut optionally, additional apertures are positioned along the length of the shaft. The number of apertures and the placement thereof on the shaft can be varied to suit larger or smaller units. Further, the apertures can be defined by round holes, slits, or other appropriate configurations. The apertures 156 thus communicate between the hollow passage 154 inside the shaft 150 and the inside of the cup 44. The water, under pressure, that is discharged through these apertures, flushes the liquid treatment materials from the cup portions and dissolves any powdered treatment materials that are used. The inlet line 48 is preferably a flexible tube which allows the line to move as the shaft 150 moves up and down.

The upper end of the shaft 150 is shaped to define a cutting blade or blades 160. A preferred cutting blade has three, generally triangular faces which meet at a point at their upper ends. The blade is preferably formed from a hardened (e.g., heat treated) stainless steel such as 304 stainless steel. Optionally, a thin coating of industrial diamond coats the cutting blades to improve wear resistance.

The shaft is slidingly received in an aligning collar or gasket 162 which is connected to the well around the opening. A sealing member, such as a seal and bushing block 164, located under the base of the well, seals around the shaft to prevent leakage of fluid from the well.

The shaft 150 is driven upwardly by a piston, such as an air cylinder 166. A mounting frame 168 supports the air cylinder at a lower end thereof and supports the bushing block 164. A computer control system 170 controls the actuation of the air cylinder 166, at appropriate times throughout the cycle, to move the shaft upwardly a preselected distance to cut the bases in turn. At the end of the cycle, the shaft is retracted from the well, allowing the empty cup 44 to be removed. The computer control system also controls the operation of other elements of the system, such as valves, pump 22, and heater 64.

A restraining member 180, pivotally connected to the wall of the sump 22 is rotated into position over the top of the cup 44. The restraining member holds the cup in the well 34 against the pressure applied by the cup cutter.

More specifically, as the cup 44 is slide into the well 34, it is restrained to a proper trajectory by side surfaces of the well and by veins 182, 184 projecting from front and rear surfaces of the well, respectively. Once the cup is positioned, the restraining member 180 can be pivoted directly over the cup manually. Alternately, as the door 14 (shown in phantom in its open position in FIG. 6B) is closed, a contact element 186 on the door contacts a corresponding contact element 188 of the restraining member 180. Preferably, a restraining member contact element 188 is a bent wire or resilient plastic element that provides limited flexibility.

Continued contact between the door contact element 186 and the restraining member contact element 188 as the door closes pivots the restraining member 180 about a pivot 190 until a portion of the restraining member, such as an extending lip 192 passes under an overhanging ledge 194 of the rear vein 184. An upstanding stop 196 engages the vein 184 to stop the restraining member from pivoting when it is directly over the cup 44. Resiliency in the contact member 188 allows it to yield functioning as a spring to hold the stop 196 against the vein 194. Optionally, a proximity switch may be mounted on the vein 184 to provide an electrical feedback signal to the control system 170 indicating that the cup is, in fact, restrained. Once the door is closed and latched, a cleaning and disinfection/sterilization cycle can be commenced.

During a cycle, the air cylinder 166 moves the shaft 150 a preselected distance upward until the cutting blade 160 punctures the base 90 of the first cup and the apertures 156 are in fluid communication with the compartment 70 of the first cup. Water pumped through the water inlet line 48 passes through the apertures and into the first compartment 70. The treatment materials in the first compartment are flushed from the compartment through the puncture hole formed by the cutting blade 160 and pass into the well 34. The treatment materials and fluid are flushed out of the well through the well outlet line 148 and are circulated through the fluid lines 24 to the nozzles 16,18. Thus, the treatment materials are thoroughly dispersed in the fluid by the time the treatment fluid reaches the nozzles. The treatment fluid is sprayed over and through the items to be cleaned and is collected in the sump 20. The cup cutter assembly 30 subsequently cuts the bases of the intermediate and inner compartments 72 and 74, respectively, in a similar manner.

In a typical cleaning and decontamination cycle, items to be cleaned and decontaminated are first inserted into the cabinet 12 through the door 14. A fresh three compartment cup 44 is inserted into the well 34 and the restraining member 182 rotated or by closing the door into the restraining position, illustrated in solid line in FIG. 6B. The controller 170 signals the valve 52 in the water inlet line 48 to open, allowing water to circulate through the fluid system 24. The controller 170 also signals the cutter assembly 30 to cut the base portion 90 of the outer cup 82. The air cylinder moves the shaft 150 a preselected vertical distance upwards until the blade 160 cuts the base 90 of the first compartment 70. Water is forced through the apertures 156 into the cup, flushing the first treatment material, such as a cleaning agent, out of the first compartment. The controller signals the heater 64 to heat the cleaning fluid to the desired temperature for effective cleaning. The cleaning fluid is sprayed through the nozzles 16 over the items to be cleaned and decontaminated. The cleaning fluid may be recirculated to the nozzles via the well 34 and fluid lines 148, 24 or passed directly to a drain.

Once sufficient water has entered the system for carrying out the cleaning part of the cycle, the controller 170 signals the valve 52 to close. The cleaning fluid removes most of the soil from the items, leaving them relatively clean, but not necessarily free of viable microorganisms.

At the end of the cleaning part of the cycle, the controller signals a drain valve 200 to open and the sprayed cleaning fluid is pumped out of the system and into a drain. Optionally, the water inlet valve 52 is opened to allow additional fresh water into the system to flush the cleaning fluid from the fluid lines and the well 34. The drain valve 200 is then closed and more water allowed into the system. The valve 52 is closed once sufficient water has been introduced.

The controller 170 signals the cutter assembly to cut the base 94 of the second cup (i.e., the lid of the first cup in the embodiment of FIGS. 2 and 3) thereby releasing the second treatment materials from the second compartment into the system. The pump 22 circulates the second treatment materials, preferably pretreatment chemicals, so that the pretreatment chemicals are distributed throughout the system and over the items to be microbially decontaminated prior to admission of the decontaminant. The buffers present buffer the water in the fluid lines to an appropriate pH (typically pH S-9) for effective decontamination. The inhibitors present coat the system and the surfaces of items to be decontaminated with traces of inhibitors to provide resistance to the corrosive effects of the decontaminant.

After a preselected period of circulation, the controller 170 signals the cutter assembly to cut the third cup base portion 118. The third treatment material, preferably the decontaminant, then mixes with the pretreatment agents in the fluid lines 24 and is sprayed through the nozzles 16 over the items to be decontaminated. A sensor 202 in fluid communication with one of the fluid flow lines 24 optionally detects the concentration of a decontaminant in the circulating fluid to ensure that a threshold concentration for effective decontamination is provided.

At the end of the cycle, the controller 170 signals the cutter assembly 30 to retract the shaft 150 to its starting position. The drain valve 200 is opened and the treatment fluid flushed from the system. Optionally, the water inlet valve 52 is opened once more to provide rinse water for rinsing the decontaminated items. The rinse water is preferably sterile to avoid recontamination of the decontaminated items.

While the system has been described with reference to spray nozzles 16, which spray the treatment fluid over the items within the chamber 12, it should be appreciated that the chamber 12 could alternatively define a receiving well in which the items are immersed in the treatment fluid. In this embodiment, the treatment fluid is flowed over the items such that interior and exterior surfaces of the items are contacted.

In the event of a premature cancellation of the cycle, the controller optionally signals the cutter to cut any remaining unopened base portions and opens the valves 52, 200 to flush the contents of the cup 44 to the drain. A valve 204 in fluid line 24 is preferably closed and the contents of the cup are flushed directly to the drain without passing through the chamber 12.

Alternatively, in the event of a canceled cycle, the cutter is retracted and the cup removed with the unopened portion or portions still intact. The three compartment cup 44 is then disposed of in a safe manner.

With reference also to FIGS. 7–12, an alternative embodiment of a sequential delivery system 230 includes a pair of delivery systems mounted side by side for independently supplying a pair of the treatment chambers 12. In this embodiment, the delivery systems are mounted outside the respective chambers 12, in fluid communication with the fluid distribution system 24. Similar parts of the second delivery system are numbered with a prime ('). For ease of reference, only one of the two delivery systems will be described in detail. It should be understood that the second delivery system operates in a similar manner. Obviously, when the decontamination system includes only one chamber 12, a single delivery system 230 will suffice.

Figure 7:
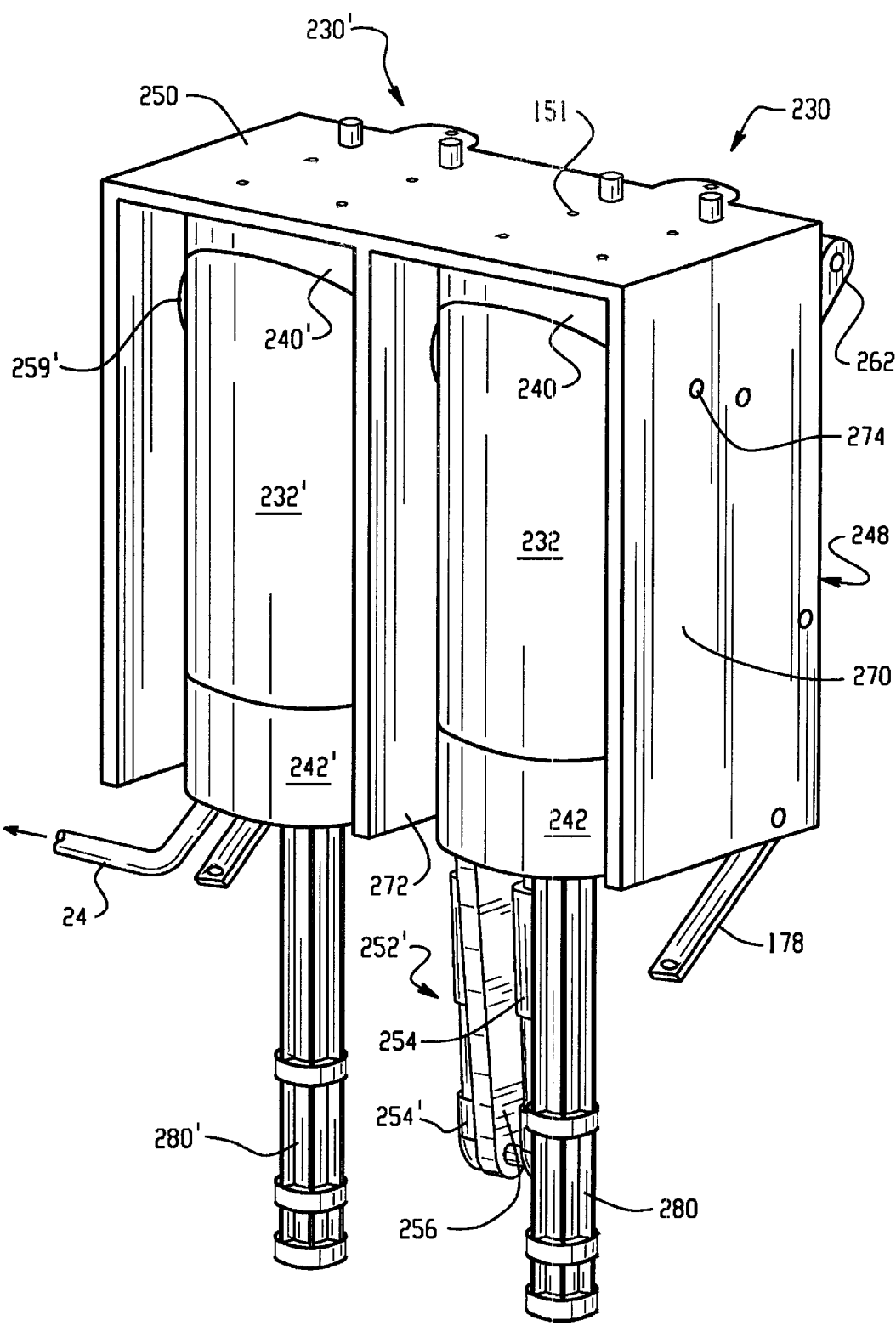
FIG. 7 is a front perspective view of an alternative embodiment of the sequential delivery assembly of FIG. 1.
Figure 8:
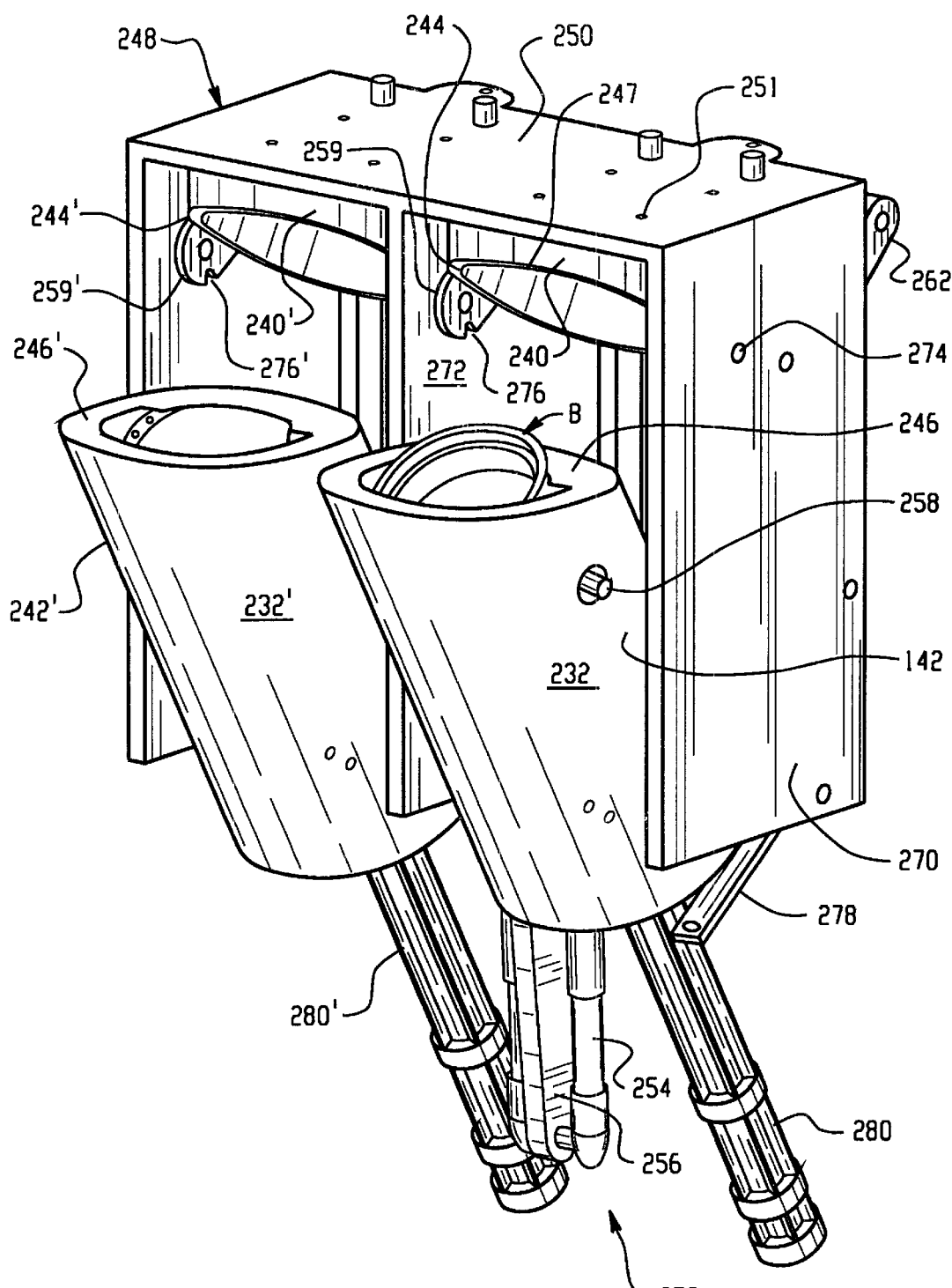
FIG. 8 is a front perspective view of the sequential delivery system of FIG. 7 with the reservoirs open for receiving treatment chemicals.
Figure 9:
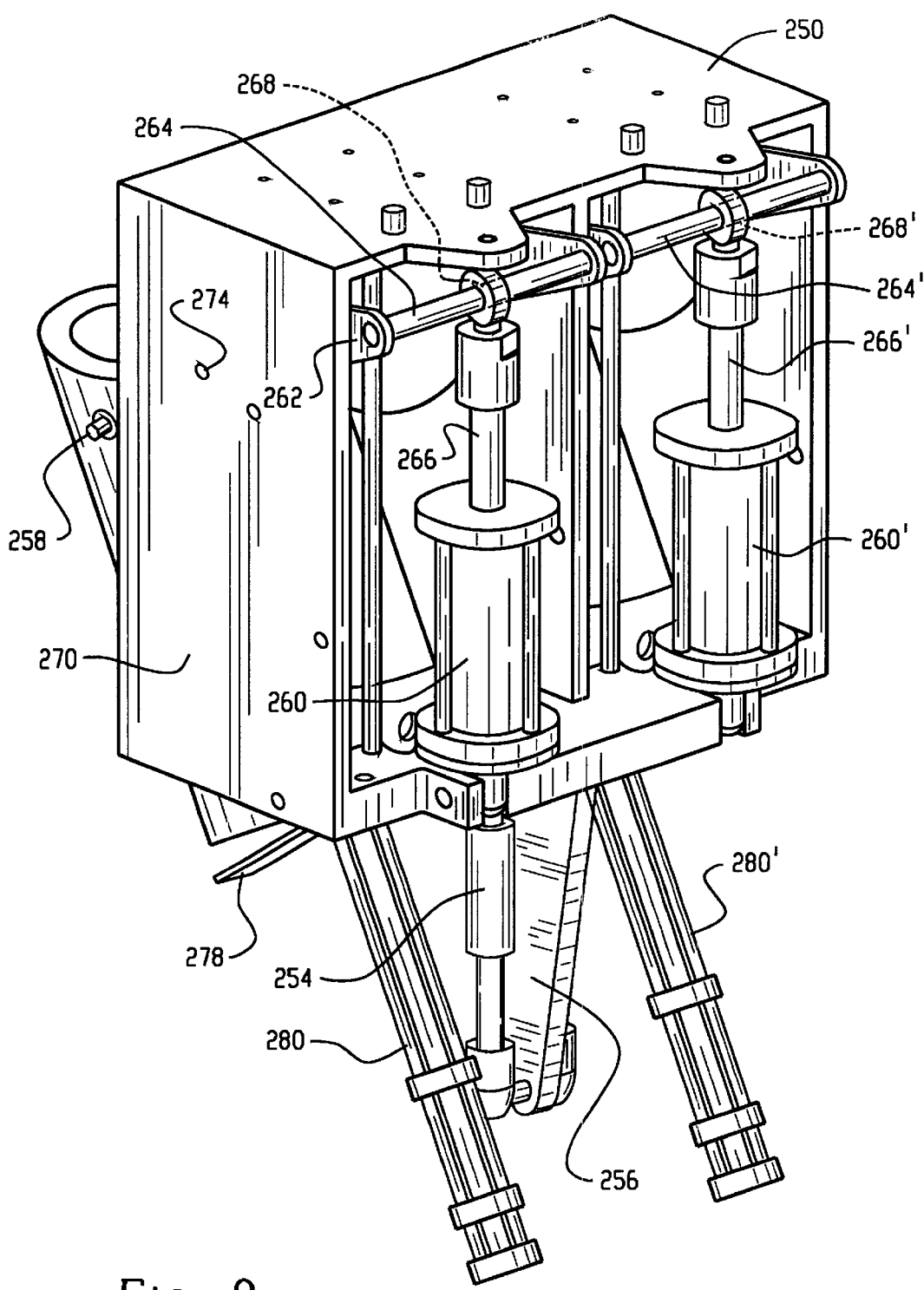
FIG. 9 is a rear perspective view of the sequential delivery assembly of FIG. 7 with the reservoirs in the open position.
Figure 10:
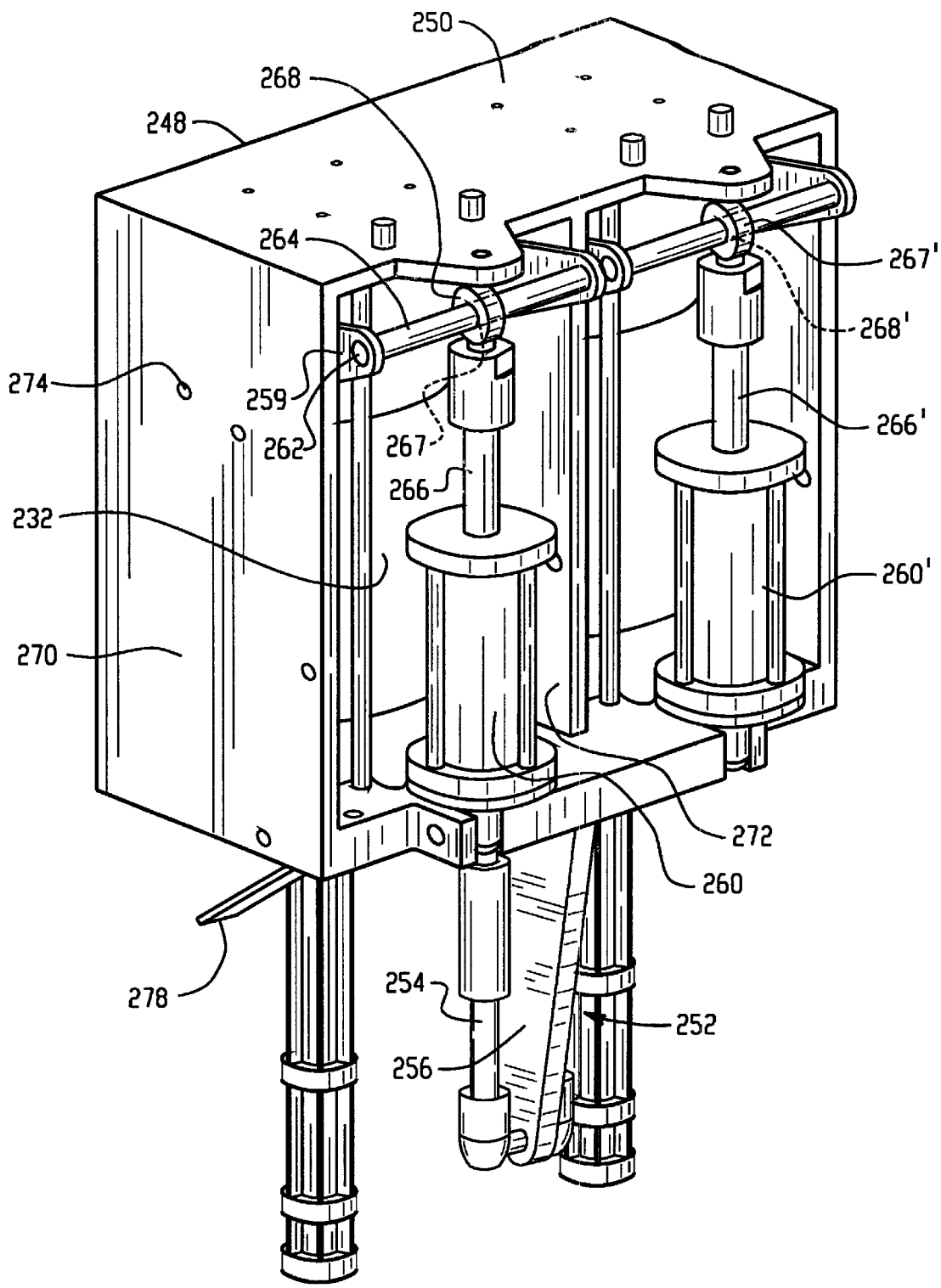
FIG. 10 is a rear perspective view of the sequential delivery assembly of FIG. 7 with the reservoirs closed.

A reservoir 232 includes an upper portion 240 and a lower portion 240 and a lower portion 242. The upper and lower portions each define the shape of a cup with a base and a cylindrical wall. Upper and lower mating or sealing surfaces 244 and 246, respectively are defined around the cup openings. The sealing surfaces meet and form a seal when the reservoir is in a closed position, as shown in FIG. 7. A sealing member, such as a gasket 247, is preferably positioned between the two sealing surfaces in the closed position. As shown in FIG. 8, the seal is positioned in a groove formed in the upper sealing surface 244, although it is alternatively positioned in a similar groove in the lower sealing surface 246. Preferably, the sealing surfaces are both angled with respect to the vertical, by an equivalent amount, so that when the reservoirs are in an open position, as shown in FIG. 8, the sealing surface 246 of the lower portion 242 defines a horizontal opening for providing easy access to the lower portion. When the reservoir is in the open position, the three compartment cup 44 may be inserted into or removed from the lower reservoir. The angled sealing surfaces 244, 246 also assist in forming an effective seal when clamped together.

Figure 11:
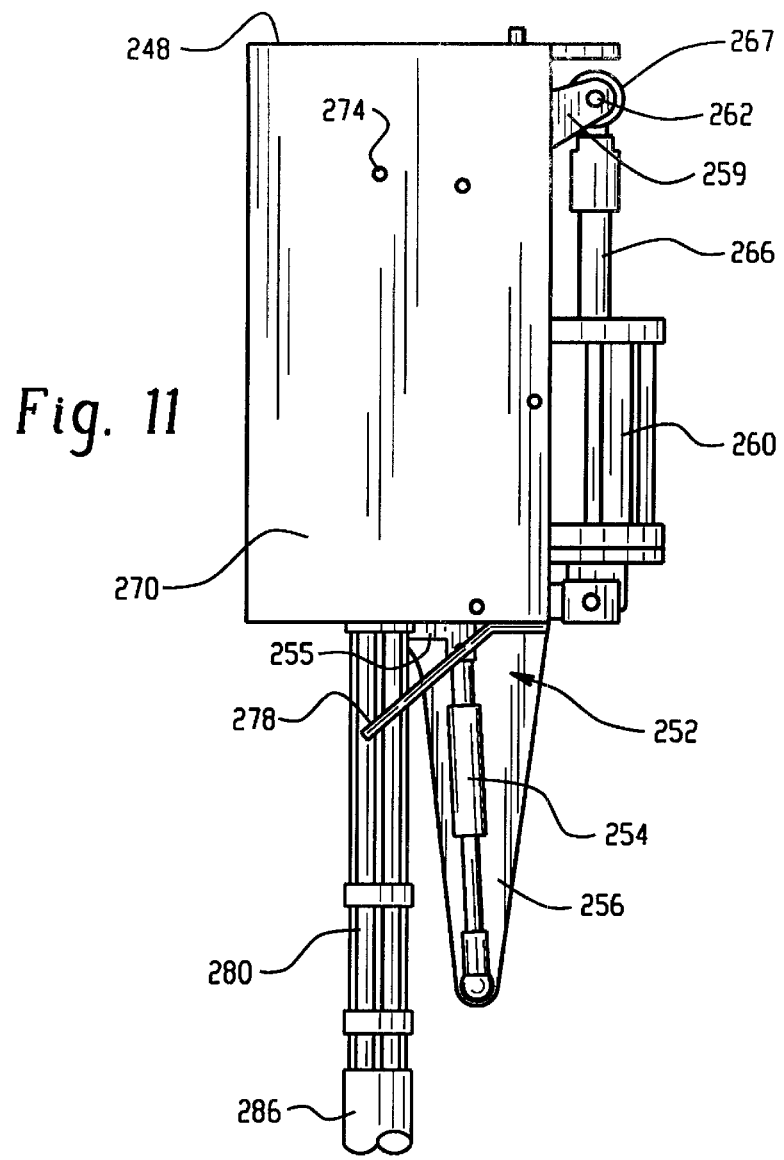
FIG. 11 is a side elevational view of the sequential delivery assembly of FIG. 7.
Figure 12:
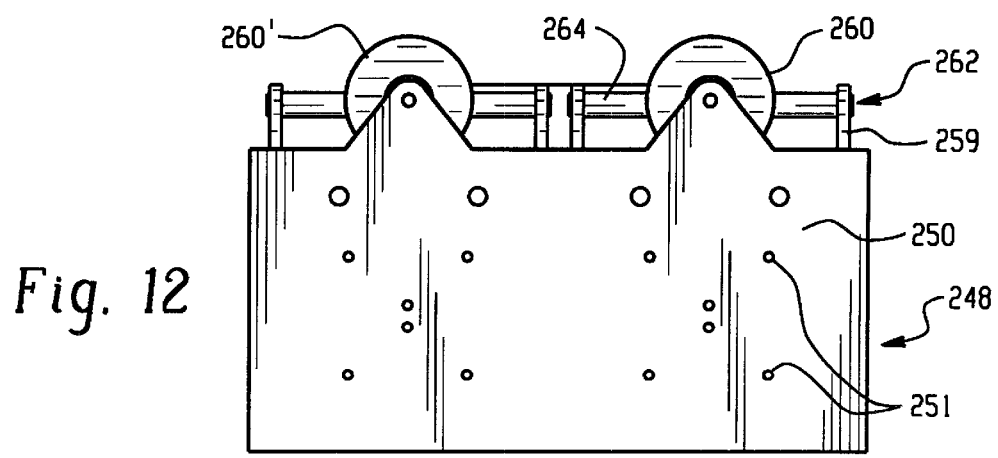
FIG. 12 is an enlarged top view of the sequential delivery assembly of FIG. 7.

The two reservoirs 232, 232' are mounted within a housing 248. The upper portion 240 of each reservoir is rigidly connected to a top wall 250 of the housing by bolts 251 or other convenient means. The lower portion 242 of the reservoir is pivotally connected to the housing by a pivoting mechanism 252 which pivots the lower portion of the reservoir into and out of the closed position. The pivoting mechanism 252 includes an air cylinder or piston 254, best shown in FIG. 11, such as a gas shock which dampens the movement of portions 242,242' during opening. As shown in FIG. 11, the gas shock is connected at an upper end to a lower surface of a pivotable bracket 255, which is pivotally mounted at a rearward end to a lower surface of the housing. The lower portions 242,242' are each supported on an upper surface of the bracket. The piston 254 is connected at a lower end to a mounting plate 256 which extends vertically downwards from the base of the housing. As the piston extends, the bracket 255 is pivoted from the open position to the closed position. The lower portions are manually moved into and out of the closed position.

A pair of locking pins 258 extend outwardly from diametrically opposite sides of an outer surface of the lower portion 242 of each reservoir, adjacent the sealing surface 246. In the closed position, the locking pins selectively engage a pair of corresponding locking cams 259 to lock the upper and lower portions together. Specifically, a locking cylinder 260, which is mounted to the rear of the housing, moves the locking cams into engagement with the respective locking pins to lock the lower portion of the reservoir in a sealing engagement with the upper portion. The pairs of locking cams 259 for each reservoir are mounted adjacent one end 262 of each cam to opposite ends of a horizontally extending locking rod 264. Each of the locking cylinders 260 includes a vertically extending cylinder rod 266 which defines a spherical rod end 267. A bore 268 defined through the cylindrical rod end receives the locking rod 264 therethrough. When the locking cylinder is activated, the cylinder rod 266 moves upward carrying with it the locking rod and the connected ends 262 of the cams 259. The cams are each pivotally connected adjacent their midpoints to vertically extending corresponding adjacent walls 270 and 272 of the housing by a pivoting member, such as a pivot pin 274. The locking cam rotates around the pivot point as the locking cylinder rod moves upward until a notch 276 defined in a lower surface of a distal end of the locking cam 259 engages the locking pin 258.

At the end of a treatment cycle, the process is reversed. The cylinder rod 266 is moved downwardly by the locking cylinder 260 to release the locking pins 258 from the locking cam 259. Then the lower portions 242 of the two reservoirs are pivoted into the open position. A stop plate 278 is rigidly mounted to a lower surface the housing, beneath the bracket 255. The stop plate arrests the downward motion of the lower portion of the reservoir in a suitable position for accessing the well.

Although the automated system shown in FIGS. 7–12 is one method of opening and closing the reservoirs 232,232', other methods are also contemplated. For example, a lid may be defined in a top surface of the reservoir which opens to allow the three compartment cup to be inserted into the reservoir. The lid is then locked in place to seal the well during a treatment cycle.

In this embodiment, the shaft 150 is driven upwardly by a vertically extending piston rod 280 which is connected to the shaft at an upper end. The piston rod is driven by an air cylinder 286 or other convenient means. The piston rod moves the shaft 280 a preselected distance upward until the cutting blade 160 punctures the base 90 of the first cup and the apertures 156 are in fluid communication with the compartment 70 of the first cup. Fluid pumped through the water inlet line 48 passes through the apertures and into the first compartment 70. The treatment materials in the first compartment are flushed from the compartment through the puncture holes formed by the cutting blades 160 and pass into the well 34. The treatment materials and fluid are flushed out of the well into the fluid system 24 by the pressure of the incoming fluid and are circulated through the fluid system 24 and the nozzles 16,18. The treatment fluid is sprayed over and through the items to be cleaned and is collected in the sump 18. The cup cutter assembly 230 subsequently cuts the bases of the intermediate and inner compartments 72, and 74, respectively, in a similar manner.

The controller 170 preferably controls the operation of the cup cutter assembly 230, locking cylinder 260, various pumps, valves, heaters and other components of the system during the running of a cleaning and decontamination cycle. At appropriate points throughout the cycle, the controller signals the cutter assembly to move the cutting shafts upward to cut one or more of the bases 90, 94, 118.

In a typical cleaning and decontamination cycle, the three compartment cup 44 is loaded into the reservoir 232. The operator pushes the reservoir lower portion into the closed position. The cams engage and lock the lower reservoir against the upper seal via actuation of cylinder 160. The controller signals the valve 52 in the water inlet line 48 to open, allowing water to circulate through the fluid lines 24. The pump 22 returns at least part of the water from the sump into the well.

Once sufficient water has entered the system for carrying out the cleaning part of the cycle, the controller 170 closes valve 33 and signals the cutter assembly 46 to cut the base portions of the cups sequentially, as for the embodiments of FIGS. 5 and 6.

At the end of the cycle, the controller 170 signals the cutter assembly 230 to retract the piston rod 280 to its starting position. The drain valve 200 is opened and the treatment fluid flushed from the system. Optionally, the water inlet valve 33 is opened once more to provide rinse water for rinsing the decontaminated items.

Various antimicrobial agents may be utilized for the decontaminant. In a preferred embodiment, the decontaminant is a solution of peracetic acid. However, it is also contemplated using other liquid or powdered decontaminants or reagents which react in a common solvent to generate peracetic acid, chlorine gas, hydrogen peroxide, hypochlorous acid, hypochlorite, or other strong oxidants which have biocidal effects.

Preferably, the pretreatment agent includes a buffer and a corrosion inhibitor. One preferred buffering system includes a combination of monosodium phosphate, disodium phosphate and tripolyphosphates. Such a buffering system also provides anticorrosion properties. Wetting agents and other corrosion inhibitors may alternatively be used. Preferred copper and brass corrosion inhibitors include azoles, benzoates, other five-membered ring compounds, benzotriazoles, tolytriazoles, mercaptobenzothiazole, and the like. Other anti-corrosive compounds include phosphates, molybdates, chromates, dichromates, tungstates, vanadates, borates, and combinations thereof.

The corrosion inhibitory agents are selected in accordance with the nature of the materials in the items being cleaned and/or decontaminated with the decontaminant. Corrosion inhibitors which protect against corrosion of aluminum and steel, including stainless steel, include phosphates, sulfates, chromates, dichromates, borates, molybdates, vanadates, and tungstates. Some additional aluminum corrosion inhibitors include 8-hydroxyquinoline and ortho-phenylphenol.

More specifically, phosphates are preferred for inhibiting stainless steel corrosion. Preferred phosphates include, but are not limited to, monosodium phosphate (MSP), disodium phosphate (DSP), sodium tripolyphosphate (TSP), sodium hexametaphosphate (HMP), and sodium sulfate either alone or in combination. Preferred borates include sodium metaborate ($NaBO_2$).

Copper and brass corrosion inhibitors include triazoles, azoles, benzoates, tolyltriazoles, dimercapto-thiadiazoles, and other five-membered ring compounds. Particularly preferred copper and brass corrosion inhibitors include sodium salts of benzotriazole and tolyltriazole which are preferred due to their stability in the presence of strong oxidizing compounds. Mercaptobenzothiazole can also be utilized but is apt to be oxidized or destabilized by strong oxidizers. Salicylic acid is an example of an acceptable benzoate corrosion inhibitor.

In hard water, phosphate buffers and corrosion inhibitors tend to cause calcium and magnesium salts present in the hard water to precipitate and coat the instruments being decontaminated and/or cleaned and also leaves deposits on parts of the system. In such cases, a sequestering agent appropriate to prevent precipitation such as sodium hexametaphosphate (HMP), or trisodium nitrolotriacetic acid (NTA $Na_3$) is preferably provided. Because sodium hexametaphosphate is also a corrosion inhibitor, it serves a dual purpose, both as a corrosion inhibitor and as a sequestering agent. Other sequestering agents include sodium polyacrylates. Of course, if soft or deionized water is utilized, the sequestering agent may be eliminated. However, to ensure universal applicability with any water that might be utilized, the presence of a sequestering agent is preferred.

A surface energy reducing agent is optionally added to the peracetic acid solution to increase penetration into crevices of items being treated. This is particularly important when cleaning and decontaminating complex medical instruments which may contain microbial contaminants in crevices, joints, and lumens. Surface energy reducing agents usable in accordance with the present invention include various wetting agents. Such wetting agents include anionic, cationic, nonionic, amphoteric, and/or zwitterionic surfactants. Specific classes of wetting agents which are useful include anionic and nonionic surfactants or combinations thereof. Examples of nonionic wetting agents usable in the present invention include surfactants such as fatty alcohol polyglycol ethers, nonylphenoxypoly (ethyleneoxy) ethanol, and ethoxylated polyoxypropylene. Specific examples include Genapol UD-50™, Igepal™, Fluowet™, and Pegal™. The wetting agents set forth above may be used alone or in combination with each other.

Amounts of the corrosion inhibitors and wetting agents to be used in the peracetic acid solution will vary depending upon the type of agent being added and whether or not one or more agents are added.

The inorganic corrosion inhibitors are preferably present in amounts ranging from about 0.01% to 20.0% weight per volume (w/v). Organic corrosion inhibitors are preferably present in amounts ranging from about 0.01% to 5.0% w/v. Phosphates are effective at concentrations in the range of about 0.01% to about 11.0% w/v.

The wetting agents are preferably present in amounts ranging from about 0.0001% to about 5.0% w/v. More preferably, the wetting agent is present in amounts ranging from about 0.0001% to about 0.5% w/v.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A system for decontaminating items, the system comprising:
   a vertical chamber for receiving the items to be decontaminated the chamber being closed by a vertical door after the items are received, the chamber having nozzles for spraying the items;
   a well defined at a bottom of the vertical chamber into which fluids drain from the items and the chamber for recirculation, the well being shaped to receive a container which includes a treatment material;
   a recirculation fluid flow path which recirculates the treatment material in liquid solution from the well to the nozzles;
   a cup cutter having a shaft extending into the well to pierce and open the container and release the treatment material;
   a restraining member within the chamber which is mounted for movement to a restraining position to prevent the container from being lifted as the shaft extends; and
   a means for assuring that the restraining member is in the restraining position during a decontamination cycle.

2. A method of delivering first and second treatment materials from a container to a chamber containing items to be decontaminated, the container including at least first and second compartments containing first and second treatment materials, the method comprising the steps of:

placing the container in a well;

closing a door to chamber;

as the door to the chamber closes, concurrently moving a restraining member across the well;

progressively advancing a shaft which successively opens the first and second compartments of the container to release the first and second treatment materials, the restraining member inhibiting the shaft from urging the container out of the well as the shaft advances to ensure that the shaft pierces the compartments as it advances; and contacting the items with solutions including the first and second treatment materials.

3. The system of claim 1, further including a drain line which selectively opens to drain the treatment solution from the system.

4. A combined system for selectively cleaning and microbially decontaminating items, the system comprising:

a container which separately contains at least a first treatment material, a second treatment material, and a third treatment material, the first treatment material including a cleaning agent, the second treatment material including a pretreatment agent including at least one of a corrosion inhibitor and a buffering system, and the third treatment material including a microbial decontaminant, the container including:

a first compartment for receiving the first treatment material, the first compartment defining a first peripheral wall;

a second compartment for receiving the second treatment material, the second compartment defining a second peripheral wall; and a third compartment for receiving a third treatment material, the third compartment defining a third peripheral wall;

a receiving well which receives the container;

a sequential delivery assembly for sequentially releasing the first treatment material, the second treatment material, and the third treatment material from the container, the sequential delivery assembly including a cup cutter which is configured for sequentially forming a first opening in the first peripheral wall, a second opening in the second peripheral wall, and a third opening in the third peripheral wall such that the first, second, and third treatment materials are released separately and sequentially;

a first fluid flow path defined between a water receiving inlet and the well for supplying water from the inlet to the well to mix with the treatment materials to form a treatment fluid, the treatment fluid sequentially including the first treatment material, the second treatment material, and at least the third pretreatment material;

a second fluid flow path being defined for the treatment fluid from the well to a cleaning and decontaminating region for receiving items to be sequentially cleaned and microbially decontaminated; and a fluid circulator for selectively circulating fluid through the first and second fluid flow paths and among the decontamination region and the receiving well.

5. The system of claim 4, wherein the cup cutter includes a shaft which defines a cutting surface for sequentially piercing the first, second, and third peripheral walls.

6. The system of claim 5, wherein the shaft defines an aperture in an exterior surface thereof, the aperture being in fluid communication with the first fluid flow path for sequentially delivering fluid to the first, second, and third compartments.

7. A combined system for selectively cleaning and microbially decontaminating items, the system comprising:

a receiving well for receiving a container which separately contains at least a first treatment material and a second treatment material, the second treatment material including a microbial decontaminant;

a cup cutter which is configured for sequentially forming a first opening in the first peripheral wall and a second opening in the second peripheral wall, the cup cutter including a shaft which defines a cutting surface for sequentially piercing the first and second peripheral walls, the shaft including a diamond coating which coats at least the cutting surface;

a first fluid flow path defined between a water receiving inlet and the well for supplying water from the inlet to the well to mix with the first and second treatment materials to form a treatment fluid, the treatment fluid sequentially including the first treatment material and the second treatment material;

a second fluid flow path being defined for the treatment fluid from the well to a cleaning and decontaminating region for receiving items to be sequentially cleaned and microbially decontaminated; and a fluid circulator for selectively circulating fluid through the first and second fluid flow paths and among the decontamination region and the receiving well.

8. The system of claim 5, wherein the at least one shaft includes a plurality of shafts, which sequentially pierce the first, second, and third peripheral walls, the plurality of shafts first simultaneously piercing the first peripheral wall, then simultaneously piercing the second peripheral wall, and then simultaneously piercing the third peripheral wall.

9. The system of claim 1, wherein the container includes:

a first compartment for receiving a first treatment material, the first compartment defining a first peripheral wall;

a second compartment for receiving a second treatment material, the second compartment defining a second peripheral wall; and a third compartment for receiving a third treatment material, the third compartment defining a third peripheral wall;

and wherein the cup cutter is configured for sequentially forming a third opening the third peripheral wall after forming a first opening in the first peripheral wall and a second opening in the second peripheral wall.

10. The system of claim 9, wherein the first treatment material includes a concentrated cleaning agent.

11. The system of claim 4, further including a plurality of nozzles, disposed within the cleaning and decontaminating region, for spraying the items with the treatment fluid, the nozzles being in fluid communication with the second fluid flow path.

12. The system of claim 4, wherein the microbial decontaminant includes a concentrated solution of peracetic acid.

13. The system of claim 9, wherein the cup cutter extends the shaft progressively upward to pierce and open the container and release first and second treatment materials separately contained in first, second, and third compartments.

14. A decontaminating system for decontaminating items, the system comprising:

a region for receiving items to be decontaminated accessed by a door;

a receiving well at the base of the region for receiving a container which contains a treatment material;

a delivery assembly for releasing the treatment material from the container into a fluid recirculation path which includes the region, the well, and recirculation lines from the well back to the chamber by way of a pump, the delivery system including a shaft extending through a passage into the well, the delivery assembly extending the shaft to pierce and open the container and release the treatment material;

a restraining member which is mounted for movement between a container receiving position and a restraining position which restrains the container from yielding without being pierced as the shaft extends; and interengaging elements on the door and the restraining member which interengage as the door is moved to its closed position to move the restraining member to the restraining position as the door closes.

15. A method of sequentially cleaning and decontaminating items, the method comprising the steps of:

opening a first compartment of a container to release a first treatment material which includes a concentrated cleaning agent;

mixing the first treatment material with water to form a first treatment fluid;

delivering the first treatment fluid to a cleaning and decontaminating region containing the items to be cleaned and decontaminated;

contacting the items to be cleaned and decontaminated with the first treatment fluid for a period sufficient to clean the items substantially of soil;

after contacting the items with the first treatment fluid, opening a second compartment of the container to release a second treatment material which includes a pretreatment material, the pretreatment material including at least one of a corrosion inhibitor and a buffering agent;

mixing the second treatment material with water to form a pretreatment solution which includes at least one of a corrosion inhibitor and a buffering system;

contacting the items to be cleaned and decontaminated and the cleaning and decontaminating region with the pretreatment solution for a period sufficient to pretreat the items and the cleaning and decontaminating region;

after contacting the items with the pretreatment solution, opening a third compartment of the container to release a third treatment material which includes an antimicrobial agent;

mixing the third treatment material with the pretreatment solution to form a second treatment fluid;

delivering the second treatment fluid to a cleaning and decontaminating region containing the items to be cleaned and decontaminated; and contacting the items to be cleaned and decontaminated with the second treatment fluid for a period sufficient to microbially decontaminate the items.

16. The method of claim 15, further including after the step of contacting the items to be cleaned and decontaminated with the first treatment fluid;

draining the first treatment fluid.

17. The method of claim 2, wherein:

the container includes a third compartment which contains a third treatment material, the step of progressively advancing the shaft including opening the third compartment, prior to opening the second compartment, to release the third treatment material; and the first treatment material includes a liquid detergent, the second treatment material includes a liquid decontaminant, and the third treatment material includes a powdered inhibitor.

18. The method of claim 15, further including prior to opening the container first compartment:

placing the items to be microbially decontaminated in a chamber which defines the cleaning and decontamination region;

placing the container in a well in the chamber; and wherein the opening steps includes:

progressively advancing a shaft which successively pierces the compartments of the container.

19. The method of claim 18, wherein as the shaft advances, the shaft tends to urge the container out of the well and further including:

as a door to the chamber closes, concurrently moving a restraining member across the well to assure that the shaft pierces the compartments as it advances.

20. A sequential delivery system comprising:

a receiving well for receiving a multi-compartment container, the container including:

a first compartment which receives a first material, the first compartment having a first wall portion, a second compartment which receives a second material, the second compartment having a second wall portion, a third compartment which receives a third material, the third compartment having a third wall portion, a sequential cutter which sequentially cuts the first wall portion, the second wall portion, and the third wall portion such that the first, second, and third materials are released sequentially;

a fluid flow path in fluid communication with the sequential cutter for selectively delivering a dilution fluid to the first, second, and third compartments to flush out the first, second, and third materials sequentially such that the first, second, and third materials are released sequentially into the dilution fluid.

21. The system of claim 20, wherein the sequential cutter includes a shaft defining a cutting surface, an opening defined in the shaft adjacent the cutting surface, and an interior bore in fluid communication with the opening and the fluid flow path.

22. The system of claim 21, wherein the sequential cutter is driven by an air cylinder.

23. The system of claim 20, further including:

a restraining member which pivots across a mouth of the well after the container has been received in the well.

24. The system of claim 23, wherein the well is defined in a lower portion of a chamber within which the items are treated sequentially with solutions formed by mixing of the dilution fluid and the first, second, and third materials, the chamber having a door which is closed after the container is received in the well and the items are received in the chamber and further including:

interacting elements connected with the door and the restraining member which pivot the restraining element across the well mouth as the door closes.

25. The system of claim 20, wherein the well is defined by:

an upper portion;

a lower portion;

a pivoted interconnection for pivotally connecting the upper and lower portions into sealing engagement to restrain the multi-compartment container from opening and out of sealing engagement to permit insertion and removal of the multicompartment container.

26. The system of claim 25, further including a pivoting mechanism which selectively pivots the lower portion into and out of sealing engagement with the upper portion.

27. The system of claim 26, wherein the sequential delivery system includes a pair of receiving wells which feed a pair of fluid flow paths, the pivoting mechanism pivoting lower portions of both wells.

28. A three compartment cup for use in a decontamination system of the type which includes a decontamination chamber for receiving items to be cleaned and decontaminated and a decontaminant receiving well in fluid communication with the chamber, the cup comprising:

a first cup portion which includes a first cup portion defining wall which defines a first compartment, the first cup portion defining wall including a first base portion, a first treatment material disposed in the first compartment, the first treatment material including a cleaning material;

a second cup portion which includes a second cup portion defining wall which defines a second compartment, the second cup portion defining wall including a second base portion, the second base portion being spaced from the first base portion, a second treatment material disposed in the second compartment, the second treatment material including a pretreatment material for preparing the decontamination system for receiving a decontaminant;

a third cup portion which includes a third cup portion defining wall which defines a third compartment, the decontaminant disposed in the third compartment, the third cup portion defining wall including a third base portion, the third base portion being spaced from the first and second base portions; the first, second, and third compartments configured for sequential opening of the first, second, and third defining walls by sequential opening of the first, second, and third base portions, such that the first treatment material, the second treatment material, and the third treatment material are sequentially and separately released.

29. The three compartment cup of claim 28, wherein the first compartment is closed by a lid which forms a portion of the peripheral wall of the second compartment.

* * * * *